United States Patent
Jeulin et al.

(10) Patent No.: US 9,562,065 B2
(45) Date of Patent: Feb. 7, 2017

(54) SUCROSE OCTASULFATES OF MAGNESIUM, PREPARATION METHOD THEREOF AND PHARMACEUTICAL COSMETIC USES OF SAME

(75) Inventors: Séverine Jeulin, Shangai (CN); Hélène Hernandez-Pigeon, Cugnaux (FR); Luc Aguilar, Escalquens (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 14/123,071

(22) PCT Filed: May 31, 2012

(86) PCT No.: PCT/EP2012/060211
§ 371 (c)(1),
(2), (4) Date: Nov. 27, 2013

(87) PCT Pub. No.: WO2012/163997
PCT Pub. Date: Dec. 6, 2012

(65) Prior Publication Data
US 2014/0121180 A1 May 1, 2014

(30) Foreign Application Priority Data
May 31, 2011 (FR) ..................................... 11 54752

(51) Int. Cl.
| C07H 11/00 | (2006.01) |
| A61K 8/60 | (2006.01) |
| A61K 31/7016 | (2006.01) |
| A61Q 19/00 | (2006.01) |
| C07H 5/10 | (2006.01) |
| A61Q 19/02 | (2006.01) |
| A61Q 19/06 | (2006.01) |
| A61Q 19/08 | (2006.01) |
| C07H 1/00 | (2006.01) |

(52) U.S. Cl.
CPC .................. *C07H 11/00* (2013.01); *A61K 8/60* (2013.01); *A61K 31/7016* (2013.01); *A61Q 19/00* (2013.01); *A61Q 19/02* (2013.01); *A61Q 19/06* (2013.01); *A61Q 19/08* (2013.01); *C07H 1/00* (2013.01); *C07H 5/10* (2013.01)

(58) Field of Classification Search
CPC ....... C07H 11/00; C07H 1/00; A61K 31/7016; A61K 8/60; A61Q 19/00
See application file for complete search history.

(56) References Cited

U.S. PATENT DOCUMENTS

| 4,098,995 A * | 7/1978 | Nair et al. .................. 536/54 |
| 5,618,798 A | 4/1997 | Bar-Shalom et al. |
| 5,908,836 A | 6/1999 | Bar-Shalom et al. |
| 2005/0112213 A1* | 5/2005 | McCullough ............ 424/686 |
| 2010/0204174 A1 | 8/2010 | Laurensou |

FOREIGN PATENT DOCUMENTS

| EP | 0640346 A1 | 3/1995 |
| FR | 2916355 A1 | 11/2008 |
| WO | WO 2006/017752 A2 | 2/2006 |

OTHER PUBLICATIONS

Banati et al, "Topical use of Sucralfate Cream in second and third degree burns", Burns, vol. 27 (2001), pp. 465-469.*
Grzesiak et al., "Changes in the Concentration of Extracellular Mg++ and Ca++ Down-Regulate E-Cadherin and Up-Regulate alpha2Beta1 Integrin Function, Activating Keratinocyte Migration on Type I Collagen" Journal of Clinical Investigation (1995) vol. 95 pp. 227-233.*
International Search Report, issued in PCT/EP2012/060211, dated Jul. 2, 2012.

* cited by examiner

*Primary Examiner* — Eric Olson
(74) *Attorney, Agent, or Firm* — Birch, Stewart, Kolasch & Birch, LLP

(57) ABSTRACT

The invention relates to a sucrose octasulfate of magnesium, having general formula I, the preparation method thereof and the use of same in the pharmaceutical and/or cosmetic field, wherein $0 \leq n \leq 4$, n is an integer and Y represents OH, Cl, Br, I, $NO_3$, $C_6H_5O_7$, $CH_3CO_2$, $CF_3CO_2$ or $-OCH_3$.

5 Claims, 1 Drawing Sheet

SUCROSE OCTASULFATES OF MAGNESIUM, PREPARATION METHOD THEREOF AND PHARMACEUTICAL COSMETIC USES OF SAME

The present invention relates to sucrose octasulfates of magnesium, the preparation method thereof and the pharmaceutical and/or cosmetic uses of same.

Oligosaccharides are carbohydrates the hydrolysis of which produces only simple sugars (monosaccharides). They are composed by the combination of at least two simple sugar molecules. Among oligosaccharides is found sucrose, formed by the condensation of two monosaccharides: one glucose molecule and one fructose molecule.

Sulfated oligosaccharides are known in the literature and have multiple biological, cosmetic and/or therapeutic activities.

For example, the application WO2006/017752 discloses a method of treating airway inflammations using sulfated oligosaccharides as active substances. Among these are found, in particular, a completely sulfated oligosaccharide resulting from the condensation of glucose and fructose.

U.S. Pat. No. 5,767,104 discloses sulfated oligosaccharides, principally sucrose octasulfate of aluminum, in the treatment of alopecia.

Furthermore, sucrose octasulfate is used as active ingredient in the treatment of gastric ulcers for its reparative/healing properties. FR 2 646 604 discloses formulations of sucrose octasulfate of aluminum, or sucralfate, with anti-inflammatory and healing properties, intended for the treatment of wounds or other ulcerous inflammations. WO 1994/00476 discloses a method of treating lesions and/or inflammations of the digestive system by administration of a sulfated sucrose salt, more particularly sucrose octasulfate of sodium or potassium.

FR 1390007 discloses the topical use of formulations containing sucralfate in combination with copper and zinc sulfate as tissue regenerating agents, healing agents and soothing agents.

Lastly, EP0230023 discloses the use of polysulfated oligosaccharides, more particularly sucrose octasulfate of potassium, as agent for healing wounds.

Problems related to cicatrization are found in a large number of pathologies, accidents or following surgical operations. There is thus a permanent need for alternative compositions that improve and/or accelerate cicatrization.

In the present invention, the inventors obtained novel compounds having surprising reparative, antimicrobial and anti-free radical properties. Indeed, surprisingly, it was shown that these compounds induce migration of keratinocytes, synthesis of hyaluronic acid, differentiation of keratinocytes and synthesis of antimicrobial peptides, unlike other metal sucrose octasulfates. Thus, these compounds help repair the skin, cure wounds and promote cicatrization in a very effective manner. Furthermore, the inventors showed that these compounds can also be used in cosmetics to maintain the comfort and beauty of the skin.

Figure 1:
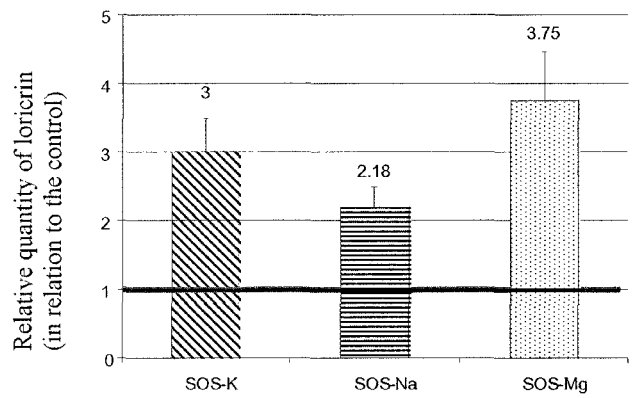
FIG. 1 represents the relative quantity of loricrin mRNA produced by keratinocytes treated for 72 hours with 30 µM sucrose octasulfate of magnesium (SOS-Mg), 30 µM sucrose octasulfate of sodium (SOS-Na) or 30 µM sucrose octasulfate of magnesium (SOS-Mg) in relation to the negative control.

The present invention relates in particular to compounds having the following general formula 1,

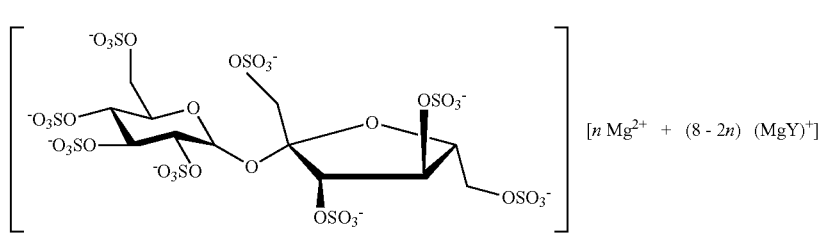

Formula I wherein:

$0 \leq n \leq 4$ n is an integer

Y represents OH, Cl, Br, I, $NO_3$, $C_6H_5O_7$, $CH_3CO_2$, $CF_3CO_2$ or $-OCH_3$.

In an embodiment of the invention, the compound of formula I according to the invention is such that n=4. This compound is represented by the following formula II.

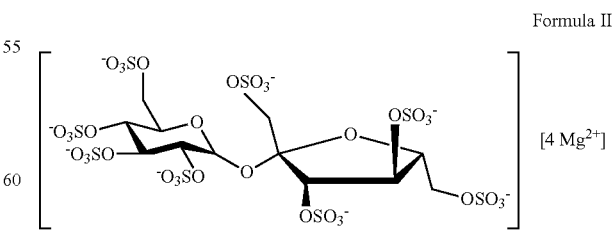

Formula II

In another embodiment of the invention, the compound of formula I according to the invention is such that n=3. This compound is represented by the following formula III.

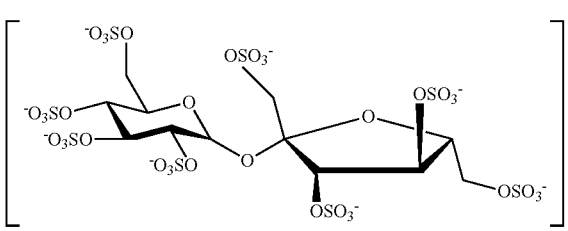

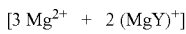

Formula III

In another embodiment of the invention, the compound of formula I according to the invention is such that n=2. This compound is represented by the following formula IV.

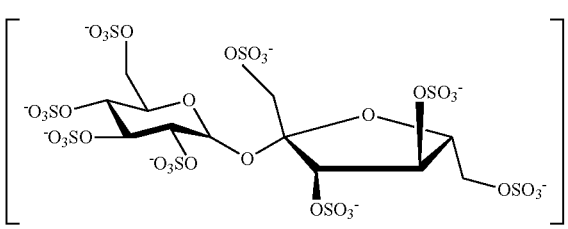

Formula IV

In another embodiment of the invention, the compound of formula I according to the invention is such that n=1. This compound is represented by the following formula V.

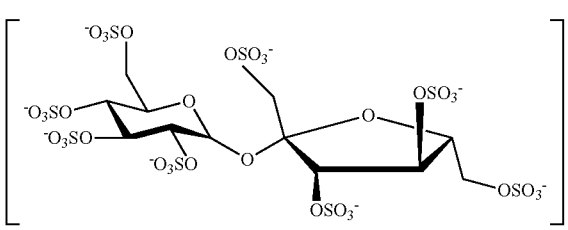

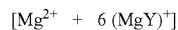

Formula V

In another embodiment of the invention, the compound of formula I according to the invention is such that n=0. This compound is represented by the following formula VI.

Formula VI

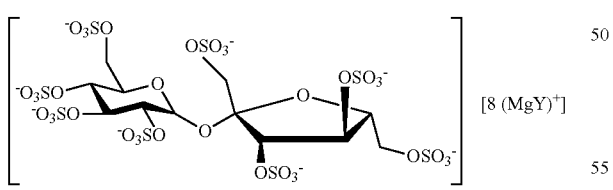

In this embodiment of the invention, the compound of formula VI corresponds to a compound of formula I wherein n is equal to 0.

In all the formulas III to VI above, Y represents OH, Cl, Br, I, NO$_3$, C$_6$H$_5$O$_7$, CH$_3$CO$_2$, CF$_3$CO$_2$ or —OCH$_3$.

Preferentially, the compound of formula according to the invention is such that n=4.

In an embodiment, the compound according to the invention is in hydrated form.

The present invention further relates to a method of preparing compounds according to the invention.

In particular, the invention relates to a method of preparing compounds of formula I according to the invention wherein it comprises the following steps:

a. placing the acid form of sucrose octasulfate in solution, preferentially in aqueous solution such as water, in contact with magnesium salt to form sucrose octasulfate of magnesium, and b. recovering the sucrose octasulfate of magnesium thus formed.

The method according to the invention thus comprises a first step a, wherein the acid form of sucrose octasulfate in solution is placed in contact with magnesium salt.

"Sucrose octasulfate in acid form" refers to sucrose octasulfate of the following formula VII:

Formula VII

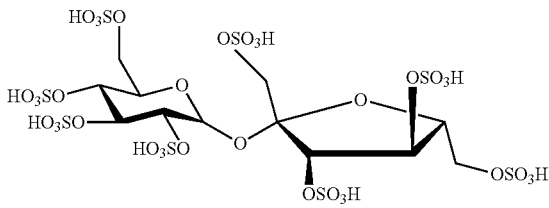

According to the invention, to "place in contact" means to bring together sucrose octasulfate in acid form and magnesium salt under conditions allowing their complexing. Preferentially, magnesium salt is dissolved in the solution of sucrose octasulfate in acid form. The relative quantities of sucrose octasulfate in acid form and of magnesium salt in the solution are selected so as to obtain the desired compound of formula I.

The contact time between sucrose octasulfate in acid form and magnesium salt can be determined by routine tests and will depend notably on the nature of the magnesium salt used. When the salt used is magnesium hydroxide, the contact time will preferentially be between 8 and 15 hours.

The placing in contact will preferentially be carried out with stirring, for example using a magnetic stirrer.

The "magnesium salt" according to the invention is preferentially selected from inorganic salts of magnesium such as, for example, $Mg(OH)_2$, $MgCl_2$, $MgBr_2$, $MgI_2$, $Mg(NO_3)_2$ or $Mg(BF_4)_2$, or an organic salt of magnesium selected from $Mg(CH_3CO_2)_2$, $Mg(CF_3CO_2)_2$, $Mg_3(C_6H_5O_7)_2$ or $Mg(CH_3O)_2$. Preferentially, the magnesium salt according to the invention is magnesium hydroxide $Mg(OH)_2$.

The mixture obtained after step a. can optionally be filtered, notably to remove possible magnesium salts which remain.

The method according to the invention comprises a second step b. wherein the sucrose octasulfate of magnesium obtained in step a. is recovered.

According to the invention, to "recover" preferentially means to obtain a sucrose octasulfate of magnesium solid, optionally a crystal.

Methods of recovering such a solid are well known to persons skilled in the art: for example, recovery according to the invention can be carried out by extraction/precipitation by addition of solvent to the mixture obtained in step a. Alternatively, it is possible to recover the solid directly by lyophilization of an aqueous solution obtained in step a. In a preferred embodiment, the solvent is added to the aqueous solution obtained in step a. and is mixed therewith. The whole is then decanted. The least dense phase containing the crystal is then recovered. This phase will preferentially be washed with water then will be lyophilized in order to obtain sucrose octasulfate of calcium in solid form.

In an embodiment, the pH of the solution obtained in step a. is adjusted to basic pH, for example pH 8.

In order to increase the yield of precipitation and purity of the compound obtained, the dense phase obtained after decantation can be dissolved in water then precipitated again in solvent. This dissolution and re-extraction in solvent can be carried out as many times as needed to obtain the desired purity and yield of sucrose octasulfate of magnesium. One such method of recovering sucrose octasulfate of calcium is notably described in the examples.

The solvent will preferentially be an organic solvent or a mixture of organic solvents such as, for example, acetone, ethanol, ethyl acetate, methyl isobutyl ketone or methyl ethyl ketone, preferentially acetone or ethanol.

The steps a. and b. are preferentially carried out in the dark.

The acid form of sucrose octasulfate in solution used in step a. of the method according to the invention can be obtained in any way known to persons skilled in the art. Preferentially, the sucrose octasulfate in acid form will be obtained from a salt of sucrose octasulfate.

In a preferred embodiment, sucrose octasulfate in acid form is obtained from a salt of sucrose octasulfate by carrying out the following steps:
   a1. dissolution in a solution, preferentially aqueous, such as water, of a salt of sucrose octasulfate,
   a2. desalification of the solution of salt of sucrose octasulfate thus obtained to form the acid form of sucrose octasulfate in solution.

The "salt of sucrose octasulfate" according to the invention can be selected from all existing salts of sucrose octasulfate such as, for example, salts of alkaline metals (such as, for example, potassium, sodium, lithium, etc.). Preferentially, the salt of sucrose octasulfate is sucrose octasulfate of potassium or sucrose octasulfate of sodium.

Step a1. makes it possible to obtain a solution of salt of sucrose octasulfate.

"Dissolution" of salt of sucrose octasulfate refers to the forming of a solution of said compound. Persons skilled in the art can easily estimate the volume of solution, preferentially aqueous, such as water, to be added to completely solubilize the desired quantity of salt of sucrose octasulfate and to obtain a solution with the required concentration (for example, between 0.01 M and 1 M). Dissolution is preferentially carried out by stirring the salt in an aqueous solution, such as water, for example, by means of a magnetic stirrer.

The method according to the invention can also comprise a step a.2 wherein the dissolved salt obtained in step a1. is desalified.

"Desalification" refers to dissociation in the salt of sucrose octasulfate of the acid form of sucrose octasulfate and the cation. This desalification step is followed by recovery of the acid form of sucrose octasulfate. This step can be carried out by any technique known to persons skilled in the art, notably by passage through an ion-exchange column.

The solution containing sucrose octasulfate acid can be passed through an ion-exchange column several times in order to eliminate all of the cations with which it is originally associated.

The ion-exchange column preferentially contains a cation-exchange resin. In an embodiment of the invention, the cation-exchange resin is a resin of the sulfonic acid type (for example, Amberlite™).

In a preferred embodiment, the method according to the invention will comprise or consist of the following steps:
   a1. dissolution in a solution of a salt of sucrose octasulfate,
   a2. desalification of the solution of salt of sucrose octasulfate thus obtained to form the acid form of sucrose octasulfate in solution.
   a. placing the acid form of sucrose octasulfate in solution in contact with magnesium salt to form sucrose octasulfate of magnesium, and
   b. precipitation of the sucrose octasulfate of magnesium thus formed.

In another embodiment, sucrose octasulfate of magnesium is obtained directly from sucralfate. Sucralfate is first sulfated, for example in pyridine, then brought together with a strong base such as $(Mg(OH)_2)$, for example.

The present invention further relates to compositions comprising one or more compounds according to the invention and at least one pharmaceutically or cosmetically acceptable excipient.

The invention also has as an object a medical device comprising one or more compounds according to the invention and a pharmaceutically or cosmetically acceptable excipient.

Preferentially, the composition according to the invention or the medical device according to the invention will contain only one type of compound of formula I, preferentially the compound of formula II.

The "excipient" according to the invention can, for example, be alone or in combination with one or more surfactants, one or more solvents, one or more water-soluble polymers, one or more thickeners or gelling agents, one or more preservatives, one or more antibacterials, one or more disinfectants, one or more healing agents, one or more antioxidants, one or more emollients and/or moisturizing agents, one or more pigments, one or more fragrances and/or one or more colorants, pH adjusters such as salts, acids, bases.

According to the invention, "pharmaceutically and/or cosmetically acceptable" refers to molecular entities and compositions that do not produce any adverse or allergic effect or other undesirable reaction when administered to an animal or human.

The exact composition and form of the composition according to the invention can be determined by persons skilled in the art according to the use and the route of administration envisaged for the composition.

The composition according to the invention will preferentially be formulated so as to be able to be administered topically or orally.

According to the invention, "topical administration" includes notably cutaneous application, oral application (oral mucosa), genital application (anal, vaginal mucosa).

According to the invention, "oral administration" includes notably administration by ingestion (including gastric).

When the composition is formulated so as to be administered topically, it will preferentially be in a form allowing ease of application such as powder, milk, cream, balm, oil, lotion, gel, foam, foaming gel, ointment, spray, paste, patch, etc. Alternatively, when anal or vaginal administration is envisaged, the composition according to the invention can be in the form of a suppository, pessary or capsule.

When the composition is formulated so as to be able to be administered in oral form it will preferentially be in the form of a gum, lozenge, tablet, drop, drinkable gel, dissolvable powder, gastric dressing, etc.

The dosages of the compounds according to the invention in the compositions will be notably determined according to the quantity of active substance necessary obtain the desired therapeutic and/or cosmetic response, according to the mode of administration envisaged and the desired treatment period.

In an embodiment, the composition according to the invention has a concentration of sucrose octasulfate of magnesium according to general formula I between 0.1 and 30% by weight. Preferentially, the composition according to the invention, for example for topical application, will comprise between 0.5 and 7%, more preferentially between 0.5 and 5% by weight of sucrose octasulfate of calcium.

The composition according to the invention can further comprise at least one other active ingredient, preferentially another healing agent, pain reliever, antiradical agent, antiseptic and/or anti-inflammatory.

The present invention further relates to compounds according to the invention or compositions according to the invention to be used as drugs.

The present invention further relates to the use of a compound or composition according to the invention for the manufacture of a drug.

The present invention further relates to a method of treatment comprising the administration to a patient in need thereof of an effective dose of compounds or compositions according to the invention Preferentially, the compounds or compositions according to the invention are used to treat the skin, mucous membranes or organs, more preferentially to promote cicatrization of the skin, mucous membranes or organs and/or to protect same from microbial infections and/or to fight microbial infections and/or to fight inflammation.

According to the invention, "cicatrization" refers notably to the phenomena of regeneration and consolidation of tissues or organs in order to cover a lesion.

"Promoting cicatrization" means notably that cicatrization occurs more rapidly and/or more effectively (absence or reduction of scars, etc.) in the presence of the compound or a composition according to the invention.

Preferentially, use according to the invention will relate to cicatrization of acute or chronic wounds and burns.

According to the invention, the expression "acute or chronic wound" includes notably abrasions, scrapes, scratches, cuts, ulcers, various wounds of the oral cavity, acne scars, blisters, cheilitis, eczema, diaper rash, dermatoporosis, ulcers, for example gastric or leg ulcers, bedsores, wounds due to diabetes (in particular of the feet), various irritations, dermatitis or scars resulting from surgery or cosmetic dermatology (laser, depilation, peeling, injection).

According to the invention, the term "burn" includes burns of any origin, including thermal, mechanical, chemical or radiation burns. Burns according to the invention can notably be radiodermatitis, burns due to the sun or to heat, or scars resulting from cryotherapy, surgery or cosmetic dermatology (laser, depilation, peeling).

"Microbial infection" refers to all infections of the skin or mucous membranes due to bacteria, yeasts, fungi or viruses. Compositions according to the invention can be used preventively to avoid the appearance of a microbial infection or therapeutically to fight an existing microbial infection.

"Inflammation" refers to an immune defense reaction of the body to an attack characterized notably by redness, swelling, a sensation of heat and pain. The present invention relates particularly to the treatment of inflammatory skin conditions.

The quantity of sucralfate to be administered to a patient will depend on the pathology to be treated and the mode of administration. For example, when gastric application is envisaged, sucrose octasulfate of calcium can be administered in a dose of 1 to 10 g/day, preferentially 2 to 6 g/day.

The present invention further relates to the use of a compound or cosmetic composition according to the invention to improve the appearance of the skin.

According to the invention, to "improve the appearance of the skin" means to improve the esthetics or comfort of a condition of the skin and/or mucous membranes.

The esthetic degradation of the condition of the skin or the comfort thereof can be due, for example to age, external conditions or variations of weight. For example, the cosmetic composition according to the invention will help restore the barrier function of the skin, moisturize the skin, increase the elasticity and/or tonicity of the skin and also reduce stretch marks, cellulitis or wrinkles as well as eliminate blotches.

Alternatively, the compound or composition according to the invention can be used in order to prevent skin aging.

The following examples are provided by way of illustration and do not limit the scope of the invention.

EXAMPLES

Example 1

Preparation of the Compound of Formula II

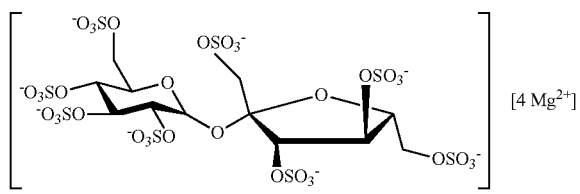

A solution of sucrose octasulfate of potassium (1.50 g; 1.16 mmol, 1.00 eq, 99%) in water (40 ml) is placed in a 100 ml round-bottom flask. The solution passed through a column (Φ 40×500 mm) containing 250 g of Amberlite IR 120 H ion-exchange resin at a rate of 1 ml/min at 0° C. The acid fraction (120 ml; pH≤1.5) is collected and neutralized immediately by the addition of magnesium hydroxide at pH=10.23. The resulting mixture is allowed to stir overnight (about 12 hours) at room temperature and pH=9.84.

The mixture is then filtered and 700 ml of acetone is added to the filtrate. The resulting mixture is allowed to rest overnight. The supernatant is decanted and the remaining syrup is dissolved in 15 ml of demineralized water, and 200 ml of acetone is added to the solution. The resulting mixture is allowed to rest for 3 hours and the supernatant is decanted. Such an operation is repeated 3 times. The syrup is then dissolved in 30 ml of water, and the mixture is lyophilized. A white solid of sucrose octasulfate of magnesium is obtained (0.50 g; 40%).

All these steps were carried out away from light by enveloping the reaction medium with aluminum foil.

Characterization of the compound of formula II obtained:

The NMR spectrum of the compound of formula II obtained is as follows: $^1$H NMR (D$_2$O, 300 MHz, ppm): δ: 4.13-4.42 (m, 9H); 4.52 (m, 1H); 4.63 (m, 2H); 5.04 (d, J=8.1 Hz, 1H); 5.73 (d, J=3.3 Hz, 1H).

Furthermore, an assay of sucrose octasulfate and magnesium contained in the compound II obtained (SOS-Mg) is carried out. The same assay is carried out with control samples having a known concentration of Mg or sucrose octasulfate: MgCl$_2$ and sucrose octasulfate of potassium (SOS-K). The assay is carried out as follows:

Standard solution and sample preparation:

5.2 mg of MgCl$_2$ (purity: 97%) weighed with precision in a 10 ml graduated flask and completely dissolved in an aqueous solution of 0.05% TFA, the final concentration being 0.504 mg/ml.

12.1 mg of SOS-K (water content: 8.82%) weighed with precision in a 10 ml graduated flask and completely dissolved in an aqueous solution of 0.05% TFA, the final concentration being 1.21 mg/ml.

16.1 mg of SOS-Mg weighed with precision in a 10 ml graduated flask and completely dissolved in an aqueous solution of 0.05% TFA, the final concentration being 1.61 mg/ml. An 8.0 ml sample is diluted with an aqueous solution of 0.05% TFA in a 10 ml graduated flask, for the analysis of sucrose octasulfate in SOS-Mg.

HPLC Analysis:

The SOS-Ca, SOS-K and CaCl$_2$ samples thus obtained are characterized by HPLC by means of the following materials and conditions: column: Atlantis T3 (4.6×100 mm; 3.0 μm), column temperature: 30° C., rate: 0.6 ml/min, injection volume: 5 μl for analysis of Mg in SOS-Mg, 20 μl for analysis of SOS in SOS-Mg, detection: ELSD ("transfer tube" temperature=50° C.; gas rate=2.0 l/min, mobile phase A: 0.05% TFA/water, mobile phase B: 0.05%/acetonitrile (gradient: T0 A: 100%, T2 A: 100%, T5 A: 5%, B: 95%).

The results obtained as for the concentration of magnesium and sucrose octasulfate are presented in the following tables 1 and 2:

TABLE 1

Estimation of the Mg concentration of the SOS-Mg sample from the MgCl$_2$ standard.

| | Concentration (mg/ml) | Mg concentration (mg/ml) | Area of the peak/Mg content |
|---|---|---|---|
| MgCl$_2$ | 0.504 | 0.1274 | 1116301 |
| SOS-Mg | 1.61 | — | 1164648 |

Calculation of the Mg concentration in the SOS-Mg sample produces a value of 3.3960 mmol/g.

TABLE 2

Estimation of the sucrose octasulfate concentration of the SOS-Mg sample from the SOS-K standard.

| | SOS concentration (mg/ml) | Area of the peak/SOS content |
|---|---|---|
| SOS-K | 0.1274 | 5322294 |
| SOS-Mg | — | 6637820 |

Calculation of the SOS concentration in the SOS-Mg sample produces a value of 0.8304 mmol/g.

As can be noted, the magnesium/sucrose octasulfate ratio in the SOS-Mg compound of formula II obtained is 3.3961/0.8304, or 4.09, which corresponds well to the expected ratio.

Example 2

Effect of Sucrose Octasulfate of Mg on Cell Migration

The migration of epithelial cells is an important step of tissue development and repair processes, such as embryogenesis and cicatrization.

The mechanisms of initiation, coordination and termination of cell movements are not completely clear, however the crucial role of cell migration is well established.

During cicatrization of skin and in dermatological chronic inflammatory affections, keratinocytes are "activated" to begin the process of migration. The cells then see their phenotype influenced by interactions with the extracellular matrix on the one hand and by cell-cell interactions on the other. Keratinocytes of the basal stratum at the edge of a wound migrate over the wound and cover it.

Indeed, keratinocytes are activated by contact with fibronectin, interstitial dermal collagen (type 1), collagen IV and laminin 5 of the basal lamina. They are also regulated by certain polypeptide growth factors such as TGFβ, TGFα and EGF. Moreover, cytokines (IL1, TNFα) and chemokines (RANTES and IL-8) also help increase the speed of reepithelialization of a wound, following keratinocyte activation.

In order to evaluate the impact of sucrose octasulfate of magnesium on the cell migration of HaCaT keratinocyte cell lines, studies were carried out using the Oris Cell Migration Assay Kit (Platypus Technologies). This study was conducted in parallel with sucrose octasulfate of potassium and sucrose octasulfate of sodium for comparison.

Biological Material

The keratinocyte cell line used is the HaCaT human keratinocytes cell line, spontaneously immortalized. This line is frequently cited as a reference model in the literature.

Cellular Migration Protocol

The protocol used for the cell migration study is based on the use of a 96-well kit, Oris Cell Migration Assay (Platypus Technologies—TEBU), enabling the miniaturization and quantification of this cell process.

The principle of this test consists in studying cell migration toward the center of the well of the 96-well plate. It consists in placing a stopper in the wells, in order to create a detection zone 2 mm in diameter. Then the stoppers are removed once the cells are well adhered to the surrounding surface, thus allowing the cells to migrate toward the detection zone. Plates without stoppers and with active agents are incubated at 37° C. for 24 hours in DMEM 0% FCS. The quantity of cells located in the zone previously occupied by the stopper is then analyzed in order to evaluate cell migration. A mask is used to visualize and count only the cells located in this zone. For each condition, an average of 4 to 8 wells is prepared.

The products tested in this study are SOS-Mg obtained in example 1 at a concentration of 10 μM, SOS-K at 10 μM (sucrose octasulfate of potassium), SOS-Na at 10 μM (sucrose octasulfate of sodium) and EGF as positive control. A negative control is prepared in which no compound is added to the culture medium (control 0% FCS).

Results

The effect of 3 sucroses was tested on the migration of HaCaT cells.

The results are quantified by means of the following formula:

$$\frac{\text{IF treated}}{\text{IF control 0\% } FCS} \times 100$$

in IF (Intensity of Fluorescence, proportional to the quantity of cells having migrated).
in percentage of activity in relation to the 0% FCS control.
The results obtained are summarized in table 3.

TABLE 3

Effect of 3 sucroses on keratinocyte migration.

|  | Control 0% FCS | EGF 33 ng | SOS-Mg 10 μM | SOS-Na 10 μM | SOS-K 10 μM |
|---|---|---|---|---|---|
| AVG IF | 5044 ± 1074 | 16138 ± 1548 | 7084 ± 662 | 4988 ± 965 | 5001 ± 835 |
| % activity/control | 100 | 320*** | 140* | 99 | 99 |

*$p < 0.05$ and
***$p < 0.001$ in relation to the 0% FCS control.

From this table it can be deduced that:
EGF at 33 ng/ml, the positive control in our experiments, induced keratinocyte migration (and proliferation) in a very large and significant manner.

at 10 μM, sucrose octasulfate of potassium and sucrose octasulfate of sodium do not induce keratinocyte migration.
at 10 μM, sucrose octasulfate of magnesium (SOS-Mg) induced keratinocyte migration in a statistically significant manner. This migration is 1.4 times greater than that induced by SOS-Na and SOS-K.

Example 3

Effect of Sucrose Octasulfate of Mg on Cell Differentiation

The epidermis plays a major protective role by providing a chemical and mechanical barrier for the body. It ensures that water-tightness is maintained, namely the skin barrier function. Corneocytes, keratinocytes of the stratum corneum, associated with a lipid matrix, provide most of this function. Nevertheless, the deeper layers act to establish the elements of this function. The ability of epidermal keratinocytes to differentiate guarantees the establishment of a barrier of the functional selective permeability type. The keratinocyte differentiation program is regulated spatiotemporally, with the deepest layers of the epidermis, the least differentiated basal layer, moving toward the stratum corneum, the ultimate stage of the differentiation of keratinocytes into corneocytes. From a cellular and molecular point of view, one principally observes the formation of keratin filaments, the transformation of keratinocytes into corneocytes, or "cornification", and the establishment of intercellular lipid cement organized in lamellar structures, ensuring water-tightness and the skin barrier function.

From a protein point of view, epidermal differentiation is mainly centered on the evolution of structural proteins, keratins, which contribute to the architectural integrity of the epidermis. Their expression varies according to the degree of keratinocyte maturation. Basic keratin 1 and acid keratin 10 are early markers of keratinocyte differentiation, present from the basal layer of the epidermis. The later expression of other markers of this biological process can be followed, such as those of cornified envelope proteins, such as corneodesmosin (CDSN), small proline-rich protein 1 (SPRR1A and SPRR1B), involucrin (IVL), as well as certain major enzymes that cause the bridging of structural proteins together and with keratinocyte lipids, transglutaminases, such as transglutaminase 1 (TGM1) or 3.

Formation of the fibrous matrix present in corneocytes is initiated at the transition between granular keratinocytes and corneocytes. Loricrin (LOR) is a structural protein containing glutamine and lysine residues which enables fixation with other proteins of the cornified envelope. Basic molecules of filaggrin (FLG), produced from its precursor profilaggrin (stored in granules of keratohyalin), associate with filaments of cytokeratin, thus enabling their aggregation. Filaggrin can then be deiminated by peptidyl-arginine deiminase (PAD) enzymes, in particular PAD1 and PAD3. Deiminated filaggrin, an acid, is then detached from intermediate filaments before being completely degraded, thus generating the amino acids that constitute natural moisturizing factor (NMF).

In parallel, synthesis and transport of keratinocyte lipids are the source of the intercorneocyte lipid cement essential to the skin barrier, the formation of which represents the ultimate phase of terminal epidermal differentiation. This extracellular lipid matrix provides the principal barrier with transcutaneous movement of water and electrolytes. Thus, a certain number of enzymes and lipid transporters see their keratinocyte expression increased with differentiation. This cement results from equilibrium between three lipid species, cholesterol, free fatty acids and ceramides. These lipids derive from glucosylceramides, sphingomyelin, cholesterol and phospholipids synthesized in the spinous and granular layers. They are transported via lamellar bodies, small secretory vesicles which combine in the granular layer and release their contents at the stratum granulosum/stratum corneum junction. In addition to these lipid precursors, lamellar bodies contain numerous enzymes including lipid hydrolases such as acid sphingomyelinase (aSmase), beta-glucocerebrosidase (GBA) or phospholipase A2 (sPLA2) as well as acid and neutral lipases. Co-delivered with lipid precursors in extracellular spaces, these enzymes convert, respectively, sphingomyelin into ceramide, beta-glucocerebroside into ceramide and phospholipids into free fatty acids and glycerol. Glucosylceramide synthase (UGCG) also intervenes in the skin lipid barrier by enabling the synthesis of glucosylceramide. Its transcription is increased during the differentiation process.

The skin barrier function also includes a defense against microorganisms. The epithelium plays an active role in the innate defenses of the host. Antimicrobial systems for the skin are based on, among other things, the presence of certain surface lipids (oleic and palmitoleic acids of sebum and certain constitutive proteins expressed more and more according to the state of differentiation of the keratinocytes (RNase 7, proteinase inhibitor 3). RNase 7 and proteinase inhibitor 3 (PI3 or elafin) have antimicrobial activities. RNase 7 is a member of the RNase A family and has broad-spectrum antimicrobial activity. It is thus capable of acting against Gram-positive or Gram-negative bacteria.

Moreover, acidification of the epidermal surface plays an important role in cutaneous antimicrobial defense. The skin thus acts not only as a physical barrier, but also as a chemical barrier. There is also an adaptive component of innate immunity based on inducible secretion of antimicrobial peptides. They have direct antimicrobial activities against various bacteria, viruses and fungi with the ability to inhibit their growth. Moreover, by their chemotactic action, these antimicrobial peptides establish the link between innate and adaptive immune responses. They play an important role as mediators of inflammation by having effects on epithelial and inflammatory cells, by influencing cell proliferation, cicatrization, cytokine and chemokine production, and chemotaxis. Antimicrobial peptides are generally synthesized in the upper layers of the spinous layer and the granular layer, but they are active in the stratum corneum where they are released. Their mode of action consists in breaking the plasma membrane of infectious microbes or penetrating the microorganism in order to interfere with intracellular metabolism. The antimicrobial peptides most studied in the skin are β-defensins and cathelicidins.

Human β-defensins constitute the major class of antimicrobial peptides found in human epithelium and four of them have been identified in the skin, hBD 1-4. Although they belong to the same family, they are regulated by different pathways.

Human β-defensin 2 (hBD-2 or DEFB4), a 4 kDa peptide bound to heparin, is one of the principal cutaneous antimicrobial peptides. Bacteriostatic only in terms of S. aureus, hBD-2 has antimicrobial activity essentially directed against Gram-negative bacteria.

β-Defensin 3 (hBD-3 or DEFB103A), a 5 kDa antimicrobial peptide, has broad-spectrum antimicrobial activity including Staphylococcus aureus.

The effect of sucrose octasulfate of magnesium and sucrose octasulfate of potassium and sodium on regulation of molecular targets involved in keratinocyte differentiation processes was evaluated. To that end, normal human keratinocytes (NHK) were brought together with the various products to be tested and the expression of various RNA coding proteins involved in the establishment of protein structures of the cornified envelope, but also in the synthesis of lipids or the expression of antimicrobial peptides, was measured.

Biological Material

The keratinocyte cell line used is the primary human keratinocyte cell line or NHKs prepared from strips of skin from cosmetic surgery waste (breast reduction). The cells are grown in low-magnesium (0.1 mM) KSFM (Invitrogen) supplemented with 25 µg/ml bovine pituitary extract (BPE) and 1.5 ng/ml epithelial growth factor (EGF).

Experimental Protocol

The products tested are 10 µM SOS-Mg, 10 µM SOS-Na, 10 µM SOS-K. In parallel, experiments are carried out with the addition of 1.2 mM $CaCl_2$ as positive control. A negative control is prepared in which no product is added to the culture medium.

The products to be tested are incubated with keratinocytes for 72 hours. The cells are then recovered and an analysis of the expression of target genes involved in epidermal differentiation is carried out using Quantigene technology, used to quantify the expression of mRNA of interest.

The values obtained by Quantigene are normalized in relation to the geometric mean of 2 reference genes, POL2RA and HPRT. Relative quantity is calculated in relation to the control. Regulation of the expression of the gene of interest is taken into account from a RQ (relative quantity)≥1.9 (induction) or RQ≥0.5 (inhibition).

Results

The effect of 3 sucrose at various concentrations was tested on keratinocyte differentiation.

A first study was undertaken on the expression of 14 genes involved in cell differentiation. The results are summarized in table 4. The values obtained are specified for genes whose expression was modified by the addition of 10 µM SOS-Mg, SOS-K or SOS-Na.

TABLE 4

Relative quantities (RQ) of mRNA expression according to the product incubated with cells in relation to the negative control.

|  | Concentration | DEFB103A | CDSN | RNASE7 | UGCG |
|---|---|---|---|---|---|
| $CaCl_2$ | 1.2 nM | 18.7 | 1.3 | 4.5 | 3.1 |
| SOS-Mg | 10 µM | 3.0 | 1.9 | 2.9 | 2.0 |
| SOS-K | 10 µM | 2.3 | 1.5 | 2.4 | 1.8 |
| SOS-Na | 10 µM | 0.9 | 0.7 | 1.6 | 1.1 |

As can be rioted in this table:

Calcium, the positive control in our experiments, induced the expression of 3 mRNA (DEFB103A, RNASE7 and UGCG).

10 μM SOS-Mg induced the expression of 4 mRNA (DEFB103A, RNASE7, CDSN and UGCG). The activity of SOS-Mg on corneodesmosin (CDSN) expression indicates that SOS-Mg participates in restoration of the protein barrier. Its activity on UGCG expression indicates its participation in restoration of the lipid barrier. Furthermore, induction of RNASE7 and DEFB103A shows the antimicrobial properties of the SOS-Mg compound.

SOS-Na did not induce the expression of any mRNA.

10 μM SOS-K induced the expression of DEFB103A, RNASE7, UGCG and CDSN to a lesser extent than SOS-Mg.

A second study was carried out under the same conditions but by measuring the expression of a larger number of genes (64 targets involved in cell differentiation) by real-time PCR.

This study shows that 30 μM SOS-Mg induced the expression of 7 mRNA (FLG, IVL, SPRR1A, SPRR1B, LOR, Padi1 and hBD2). These inductions show the role of SOS-Mg in the induction of keratinocyte differentiation and thus of cicatrization (IVL, SPRR1A, SPRR1B and LOR), in moisturization (Padi1) as well as its antimicrobial properties (hBD2).

Figure 2:
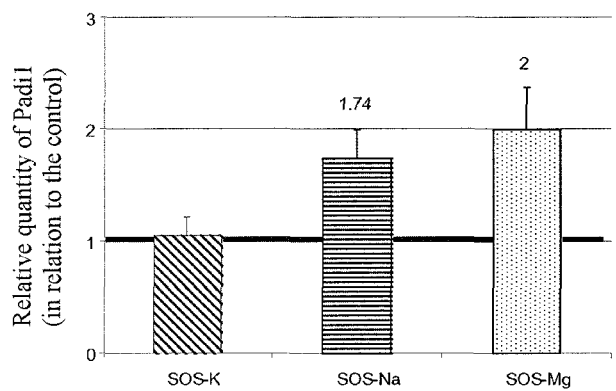
FIG. 2 represents the relative quantity of Padi1 mRNA produced by keratinocytes treated for 72 hours with 30 µM sucrose octasulfate of magnesium (SOS-Mg), 30 µM sucrose octasulfate of sodium (SOS-Na) or 30 µM sucrose octasulfate of magnesium (SOS-Mg) in relation to the negative control.
Figure 3:
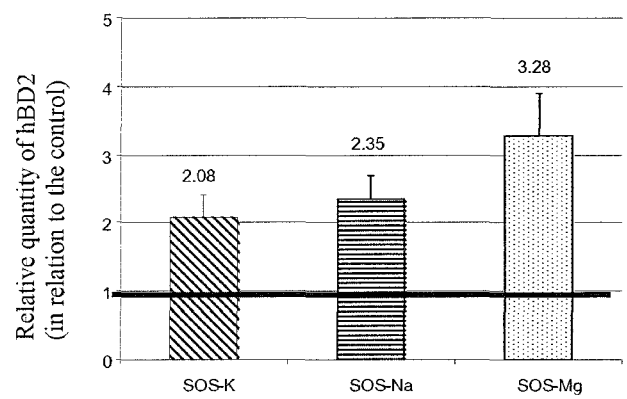
FIG. 3 represents the relative quantity of hBD2 mRNA produced by keratinocytes treated for 72 hours with 30 µM sucrose octasulfate of magnesium (SOS-Mg), 30 µM sucrose octasulfate of sodium (SOS-Na) or 30 µM sucrose octasulfate of magnesium (SOS-Mg) in relation to the negative control.

In order to compare the effects of SOS-Mg, SOS-Na and SOS-K in three functions important for cicatrization: cell differentiation, moisturization and antimicrobial properties, the induction of 3 genes, loricrin, Padi1 and hBD2 (DEFB4), by SOS-Mg, SOS-Na and SOS-K were compared. The results are presented in FIGS. 1 to 3.

It can be noted that loricrin, Padi1 and hBD2 (DEFB4) were induced to a greater extent by SOS-Mg than SOS-Na and SOS-K. SOS-Mg thus induces keratinocyte differentiation and promotes formation of a physical barrier and antimicrobial function as well as moisturization of the skin.

The invention claimed is:

1. A method of promoting cicatrization, which comprises: administering topically to a patient in need thereof an effective dose to repair skin of a composition including an excipient and a compound having general formula I

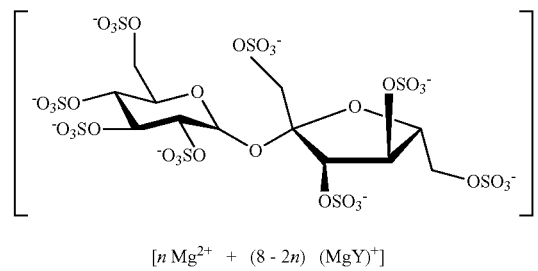

Formula I $$[n\,Mg^{2+} + (8 - 2n)\,(MgY)^+]$$

wherein:
n=4
n is an integer
Y represents OH, Cl, Br, I, $NO_3$, $BF_4$, $C_6H_5O_7$, $CH_3CO_2$, $CF_3CO_2$ or —$OCH_3$,
  wherein the compound having general formula I is at a concentration of between 0.5 and 30% by weight with respect to the composition.

2. The method according to claim 1, wherein cicatrization is promoted for the treatment acute or chronic wounds.

3. The method according to claim 2, wherein the burns and acute or chronic wounds are due to abrasions, scrapes, scratches, cuts, wounds of the oral cavity of various origin, acne scars, cryotherapy scars, scars resulting from surgery or cosmetic dermatology.

4. The method according to claim 1, wherein the effective dose is 1 to 10 g/day of the compound having general formula I.

5. The method according to claim 1, wherein cicatrization is promoted for the treatment of acute wounds.

* * * * *